Figures 1, 2:
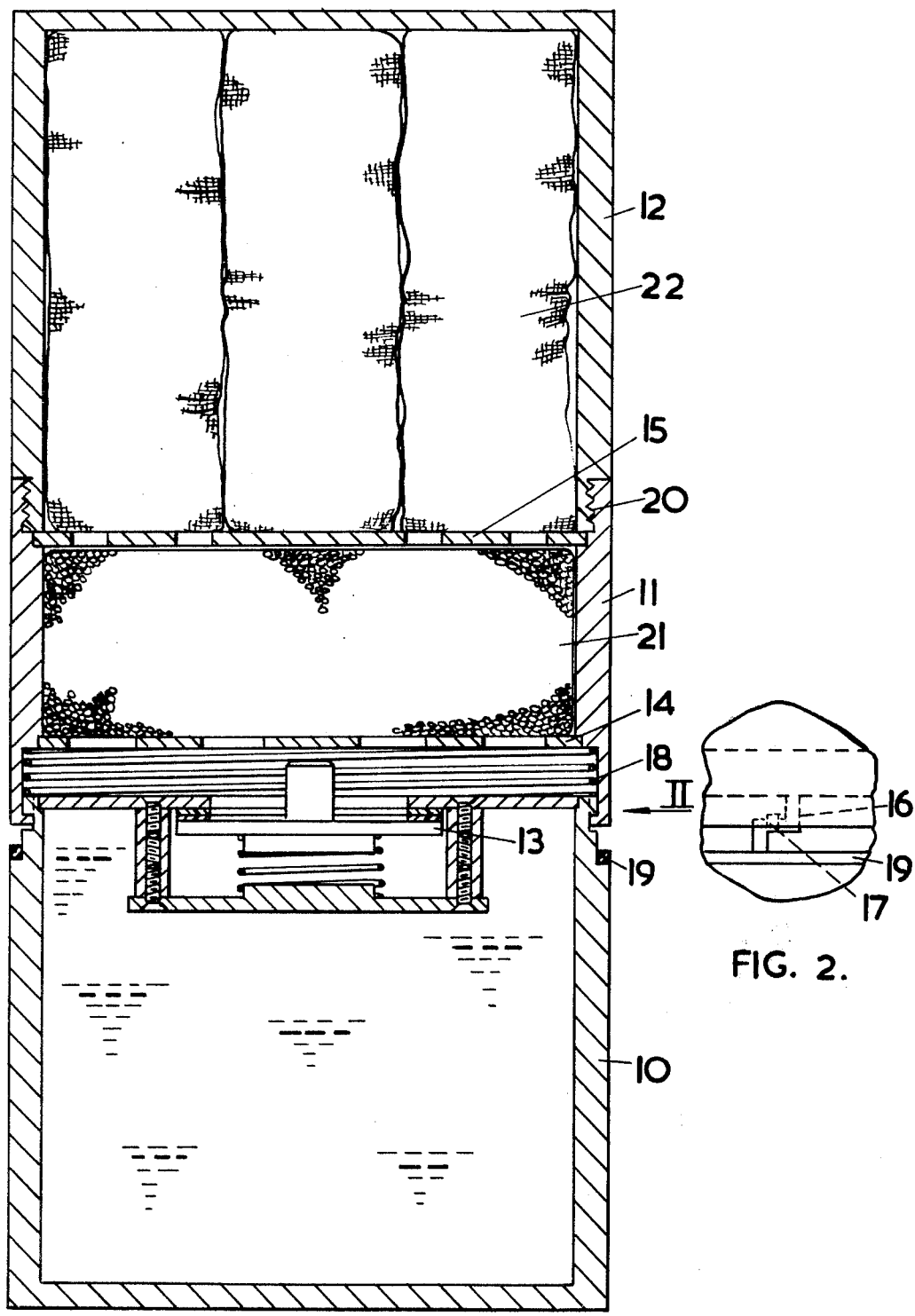

United States Patent [19]

Bourne et al.

[11] 4,011,945
[45] Mar. 15, 1977

[54] FIRST AID EQUIPMENT

[75] Inventors: Edmund Alexander Bourne, Farnborough; James Gerard Fitzgerald, London, both of England

[73] Assignee: National Research Development Corporation, London, England

[22] Filed: Sept. 9, 1975

[21] Appl. No.: 611,686

[30] Foreign Application Priority Data

Sept. 13, 1974 United Kingdom ............. 40128/74

[52] U.S. Cl. .............................. 206/223; 206/221; 206/803; 206/440; 128/403; 215/DIG. 8
[51] Int. Cl.² .................. A61B 19/02; B65D 69/00
[58] Field of Search .......... 206/803, 216, 223, 440, 206/219–222; 128/399, 403, 400, 156; 215/DIG. 8

[56] References Cited
UNITED STATES PATENTS 2,615,443  10/1952  Sukaccu ........................... 126/263
3,392,826  7/1968  Powlan ............................ 206/222

FOREIGN PATENTS OR APPLICATIONS 1,383,536  2/1975  United Kingdom ............. 128/403

Primary Examiner—William Price
Assistant Examiner—Douglas B. Farrow
Attorney, Agent, or Firm—Cushman, Darby & Cushman

[57] ABSTRACT

A cold, wet bandage dispenser for use in the treatment of burns, comprising a reservoir for water, a compartment for absorbent dressing and a compartment for a non-toxic endothermic reactor, the dispenser being operable to allow the water to pass through the reactor compartment, and be cooled by reaction with the reactor, and to pass into the absorbent dressing compartment.

15 Claims, 2 Drawing Figures

U.S. Patent  Mar. 15, 1977  4,011,945

FIRST AID EQUIPMENT

The present invention relates to first aid equipment for the treatment of burns.

It is now well known that a first aid treatment for burns to human or animal tissue which includes immersion in cold water is highly effective in preventing tissue damage and in reducing so-called "shock" effects. The cooler the water is the better, and indeed immersion in snow or ice is understood to be a recommended first aid treatment in Iceland.

The present invention provides a first aid kit whereby a portion of a human or animal body which has been burnt can readily and quickly be immersed in cold water.

According to the present invention a first aid kit for treating burns to human or animal tissue comprises a reservoir for water and a compartment or compartments containing absorbent dressing and non-toxic endothermic reactor, the reservoir being normally sealed from the compartment or compartments but being rapidly openable to allow water into the compartment or compartments, and the arrangement beng such that when the kit is charged the reservoir may be opened to allow water to the compartment or compartments at will to be cooled by reaction with the reactor and to be absorbed by the dressing.

The dressing may be impregnated with the reactor. According to a feature of the invention, however, the kit may have two compartments in addition to the reservoir, the first arranged for communication with the reservoir when open and the second communicating with the first, the first compartment being adapted to contain the reactor and the second being adapted to contain the dressing, and the compartments being openable for the removal of the dressing and recharging with dressing and reactor.

In a typical embodiment of the invention the kit has a reservoir and first and second compartments in line, the reservoir forming the base of the kit and having in the top thereof a spring loaded valve normally sealing the container, the first compartment associated with the reservoir in such a way as to be both detachable therefrom to permit charging the reservoir with water and operable with respect thereto to open the valve, the first compartment being accessible to permit charging with a non-toxic endothermic reactor and being adapted both to retain the reactor and to allow water therethrough into the second compartment, and the second compartment being adapted to contain absorbent dressing and being readily openable to permit charging with and removal of the dressing. Preferably the first compartment has perforated end walls and the second compartment is adapted to contain water when inverted. Thus in operation of the charged kit, it is inverted, the first compartment is operated with respect to the reservoir to permit water to pass through the first compartment reacting with the reactor whereupon it loses heat, and into the second compartment where some at least of it is absorbed by the dressings. The kit may then be restored to its normal configuration to drain excess cooled water back into the reservoir and the second compartment opened to remove and use the wetted chilled dressing.

While the kit need not be completely air tight, it is advantageous that at least atmosphere is prevented from affecting the reactor or the dressing. The reservoir however may be sealed sufficiently to prevent loss of its contents by evaporation or spilling. The kit may be made of a plastics material.

A suitable dressing normally includes rolls of bandage, though pads of lint may be used alternatively or additionally.

The non-toxic endothermic reactor may comprise anhydrous crystals which take up heat on dissolving in water. A particularly suitable reactor is urea which is somewhat antiseptic and can be formed into a tablet by compressing crystals thereof together, the tablet being readily soluble in water. Such a tablet having a volume ratio of 1:2, and a weight ratio of 1:4–5, with respect to the water, is capable of producing a drop in temperature of 10° to 15° C in the water. Suitable tablets may be supplied as refills to the first compartment. Alternatively permeable bags containing the reactor in loose crystal or pellet form may be employed.

The water may be ordinary tap water. As it is possible that the kit may stand charged for a period of years a preservative such as phenol may be prescribed for addition to the water. In the kit the water is likely to attain the temperature of its environment before long, e.g. 20° C. A kit in accordance with the invention can thus be used to soak rapidly bandages with water cooled to about 5° C for application to burns on human or animal tissue.

An embodiment of the invention will now be described by way of example with respect to the accompanying drawings, of which:

FIG. 1 is a sectional view of a burns first aid kit, and
FIG. 2 is a detailed view on 2 in FIG. 1.

As shown in FIG. 1 the kit is a cylindrical assembly of three separable compartments, these being a reservoir tin at the base, a first compartment 11 and a second compartment 12. A spring loaded valve 13 in the top of the reservoir 10 normally seals the reservoir. The first compartment 11 is half the volume of the reservoir and has perforated end walls 14, 15 on which the lower wall 14 is positioned and adapted for operation of the valve 13 and the upper wall 15 is removable.

The first compartment is attached to the reservoir by bayonet means 16 which have an interim stop 17 (see FIG. 2). A spring 18 preferably plastic coated, urges the compartment 11 away from the reservoir and hence the wall 14 away from the valve 13. A rubber washer 19 serves to prevent spillage of water during operation.

The second compartment 12 is about the same volume as the reservoir and is attached to the first by coarse multi-start screw thread means 20.

The kit is prepared for use by pouring water into the reservoir 10 through the valve 13, with the reservoir detached from the first compartment. A few drops of phenol are added to preserve the water. With the valve closed the top of the reservoir is wiped dry and the first compartment is fitted to the reservoir, so that the interim stops 17 of the bayonet means are engaged.

With the second compartment detached from the first and the end wall 15 removed, a tablet 21 of compressed urea is loaded into the first compartment. The wall 15 is replaced, a plurality of absorbent bandages 22 are stood upon it, and the second compartment is re-attached to the first.

To use the kit it is inverted and with the bayonet means withdrawn from the interim stop 17 the reservoir is compressed towards the first compartment until the latter bears on the washers 19. Water leaves the reservoir and in dissolving the urea in the first compartment is chilled before being absorbed by the bandages. Shaking may speed up the reaction. When it appears that the bandages have absorbed a fair amount of water the kit can be righted for excess water to return to the reservoir and the compression released. The second compartment 12 is unscrewed from the first and the bandages are then available for application to the wound.

A typical kit as described has an overall length of about 23 cm and a diameter of 11 cm, with a reservoir 9 cm long and a final compartment 4 cm long. The reservoir will hold about 900 grammes of water, and the first compartment a tablet formed by compressing about 200 grammes of urea crystals with a force of about 20 psi. This will be capable of chilling the water by 10°–15° C. The second compartment will hold about five 8 cm broad 3 cm diameter absorbent roller bandages. Such a kit may be suitable for mounting in an ambulance, fire tender, or first aid room. A smaller kit capable of carrying three such bandages may be more suitable for domestic use. The kit may be supplied with spare charges of urea, bandages and phenol.

It will be appreciated that the above embodiment has been described by way of example only. Many variations may occur to those skilled in the art. For example the valve may be arranged for direct external operation, to close or open it or both, or be gravity or acceleration operated, and the detachment of the first compartment from the reservoir obviated. The bayonet means illustrated are preferred for quick operation and for being arranged to prevent unwanted opening of the valve in storage or separation of the kit in use. However a coarse thread or other means may be employed. If it is required to prevent even the small incursion of moisture to the compartments permitted in the illustrated example, a waterproof sleeve may be fitted bridging either or both of the joints.

Insofar as solution remains in the final compartment after removal of the bandages, this may be evaporated to recover some of the urea.

I claim:

1. A first aid kit for treating burns to human or animal tissue and comprising a reservoir for water and a compartment or compartments containing absorbent dressing and non-toxic endothermic reactor, the reservoir being normally sealed from the compartment or compartments but being rapidly openable to allow water into the compartment or compartments, and the arangement being such that when the kit is charged the reservoir may be opened to allow water to the compartment or compartments at will to be cooled by reaction with the reactor and to be absorbed by the dressing.

2. A first aid kit as claimed in claim 1 and having two compartments in addition to the reservoir, the first arranged for communication with the reservoir when open and the second communicating with the first, the first compartment being adapted to contain the reactor and the second being adapted to contain the dressing, and the compartments being openable for the removal of the dressing and recharging with dressing and reactor.

3. A first aid kit for treating burns to human or animal tissue and comprising a reservoir and first and second compartments in line, the reservoir forming the base of the kit and having in the top thereof a spring loaded valve normally sealing the container, the first compartment associated with the reservoir in such a way as to be both detachable therefrom to permit charging the reservoir with water and operable with respect thereto to open the valve, the first compartment being accessible to permit charging with a non-toxic endothermic reactor and being adapted both to retain the reactor and to allow water therethrough into the second compartment, and the second compartment being adapted to contain absorbent dressing and being readily openable to permit charging with and removal of the dressing.

4. A first aid kit as claimed in claim 3 and wherein the first compartment has perforated end walls and the second compartment is adapted to contain water when inverted.

5. A first aid kit as claimed in claim 3 and wherein the reactor comprises anhydrous crystals which take up heat on dissolving in water.

6. A first aid kit as claimed in claim 3 and wherein the reactor comprises urea.

7. A first aid kit as claimed in claim 3 and wherein the reactor is in tablet form.

8. A first aid kit as claimed in claim 3 and wherein the first compartment is attached to the reservoir by bayonet means.

9. A first aid kit as claimed in claim 3 and wherein the second compartment is attached to the first by a coarse multi-start screw thread.

10. A first aid kit as claimed in claim 3 and wherein the water contains a preservative.

11. A first aid kit as claimed in claim 3 and wherein the reservoir and first compartment are adapted to hold water and reactor respectively in a weight ratio of between 4 and 5:1.

12. A first aid kit as claimed in claim 3 and wherein the second compartment is adapted to hold about five 8 cm broad roller bandages in 3 cm diameter rolls.

13. A first aid kit for treating burns to human or animal tissue and comprising a reservoir and first and second compartments in line, the reservoir forming the base of the kit and having in the top thereof a spring loaded valve normally sealing the container, the first compartment having perforated end walls and associated with the reservoir in such a way as to be both detachable therefrom to permit charging the reservoir with water and operable with respect thereto to open the valve, the first compartment being accessible to permit charging with a non-toxic endothermic reactor and being adapted both to retain the reactor and to allow water therethrough into the second compartment, and the second compartment being adapted to contain absorbent dressing and being readily openable to permit charging with and removal of the dressing and adapted to contain water when inverted, the first compartment being attached to the reservoir by bayonet means and the second compartment being attached to the first by a coarse, multi-start screw thread.

14. A first aid kit for treating burns to human or animal tissue and comprising a reservoir and first and second compartments in line, the reservoir forming the base of the kit and having in the top thereof a spring loaded valve normally sealing the container, the first compartment having perforated end walls and associated with the reservoir in such a way as to be both detachable therefrom to permit charging the reservoir with water and operable with respect thereto to open the valve, the first compartment being accessible to permit charging with a non-toxic endothermic reactor and being adapted both to retain the reactor and to allow water therethrough into the second compartment, and the second compartment being adapted to contain absorbent dressing and being readily openable to permit charging with and removal of the dressing and wherein the reactor comprises anhydrous crystals of urea and the reservoir and first compartment are adapted to hold water and reactor respectively in a weight ratio of between 4 and 5:1.

15. A first aid kit comprising:

closed compartment means housing at least one dry, water-absorbent bandage in communication with a quanta of anhydrous urea;

wall means providing a reservoir with filling of water, annexed to the closed compartment means;

normally closed, openable valve means between the reservoir and the compartment, for permitting admission of said water from the reservoir through the valve means to the compartment for endothermic hydration of the urea and a chilling soaking of the bandage; and wall means providing access to the compartment means for permitting withdrawal from the compartment means of the soaked bandage.

* * * * *